(12) United States Patent
Hoffman

(10) Patent No.: US 12,099,960 B2
(45) Date of Patent: Sep. 24, 2024

(54) METHODS AND SYSTEMS FOR FILLING CLIMATE CONTROLLED MEDICATIONS

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 18/386,804

(22) Filed: Nov. 3, 2023

(65) Prior Publication Data

US 2024/0062139 A1 Feb. 22, 2024

Related U.S. Application Data

(62) Division of application No. 17/062,266, filed on Oct. 2, 2020, now Pat. No. 11,842,316.

(60) Provisional application No. 62/910,837, filed on Oct. 4, 2019.

(51) Int. Cl.
*G06Q 10/0832* (2023.01)
*A61J 1/16* (2023.01)
*G16H 20/13* (2018.01)

(52) U.S. Cl.
CPC .......... *G06Q 10/0832* (2013.01); *A61J 1/165* (2013.01); *G16H 20/13* (2018.01)

(58) Field of Classification Search
CPC ............. G26H 20/13; A61J 1/165; F25D 3/08
See application file for complete search history.

(56) References Cited

U.S. PATENT DOCUMENTS

| | | | |
|---|---|---|---|
| 4,262,494 | A | 4/1981 | Karow, Jr. |
| 5,417,082 | A | 5/1995 | Foster |
| 5,441,170 | A | 8/1995 | Bane, III |
| 5,827,385 | A | 10/1998 | Meyer |
| 5,924,302 | A | 7/1999 | Derifield |
| 5,956,968 | A | 9/1999 | Grabowski |
| 5,979,693 | A | 11/1999 | Bane, III |
| 6,397,163 | B1 | 5/2002 | Hoyt |
| 6,536,189 | B1 | 3/2003 | Murray |

(Continued)

FOREIGN PATENT DOCUMENTS

| | | |
|---|---|---|
| CN | 2172444 Y | 7/1994 |
| EP | 1107150 A2 | 6/2001 |

OTHER PUBLICATIONS

"The Cold Chain: Part Two", Winter 2013, Pharmacy Connection, 3 pages (Year: 2013).

(Continued)

*Primary Examiner* — Elizabeth J Martin
(74) *Attorney, Agent, or Firm* — Dickinson Wright PLLC

(57) ABSTRACT

A temperature-controlled medication packaging system includes a storage with a temperature-controlled interior containing at least one medication. The packaging system further includes at least one shipping container and at least one coolant that is sized to fit within the at least one shipping container. A first robot is adapted to retrieve the at least one medication from the storage and transport the at least one medication to a second robot. The second robot is adapted to receive the at least one medication from the first robot and to bring the at least one medication and the at least one shipping container and the at least one coolant together for packaging.

20 Claims, 8 Drawing Sheets

(56) References Cited

U.S. PATENT DOCUMENTS

| | | |
|---|---|---|
| 6,868,982 B2 | 3/2005 | Gordon |
| 6,875,486 B2 | 4/2005 | Miller |
| 6,886,357 B2 | 5/2005 | Gano, III |
| 6,968,711 B2 | 11/2005 | Smith |
| 7,028,504 B2 | 4/2006 | Derifield |
| 7,130,771 B2 | 10/2006 | Aghassipour |
| 8,050,942 B1 | 11/2011 | Ali |
| 8,600,903 B2 | 12/2013 | Eller |
| 8,707,658 B2 | 4/2014 | Schäfer |
| 9,518,873 B2 | 12/2016 | Bellamkonda |
| 9,938,034 B2 | 4/2018 | Atkinson |
| 10,598,410 B2 | 3/2020 | Moon |
| 10,625,922 B2 | 4/2020 | Epenetos |
| 10,643,170 B2 | 5/2020 | Lee |
| 10,909,492 B1 | 2/2021 | Reinhardt |
| 10,916,340 B2 | 2/2021 | Hawkes |
| 2002/0004724 A1 | 1/2002 | Eastman |
| 2003/0014994 A1 | 1/2003 | Smith |
| 2004/0200232 A1 | 10/2004 | Gano, III |
| 2004/0243353 A1 | 12/2004 | Aghassipour |
| 2007/0028642 A1 | 2/2007 | Glade |
| 2007/0193297 A1 | 8/2007 | Wilson |
| 2008/0308452 A1 | 12/2008 | Eller |
| 2011/0022532 A1 | 1/2011 | Kriss |
| 2012/0248101 A1* | 10/2012 | Tumber .................... F25D 3/08 53/473 |
| 2013/0340390 A1* | 12/2013 | Carson ................ G07F 17/0092 53/473 |
| 2014/0156064 A1 | 6/2014 | Crawford |
| 2014/0352334 A1 | 12/2014 | Barakat |
| 2019/0195547 A1 | 6/2019 | Moon |
| 2020/0090803 A1 | 3/2020 | Kircher |
| 2020/0126031 A1 | 4/2020 | Whalen |
| 2020/0198823 A1 | 6/2020 | Bauer |

OTHER PUBLICATIONS

An Overview: Storage of Pharmaceutical Products, Oct. 2013; vol. 2, Issue 5, 2499-2515, World Journal of Pharmacy and Pharmaceutical Sciences, 18 pages (Year: 2013).

* cited by examiner

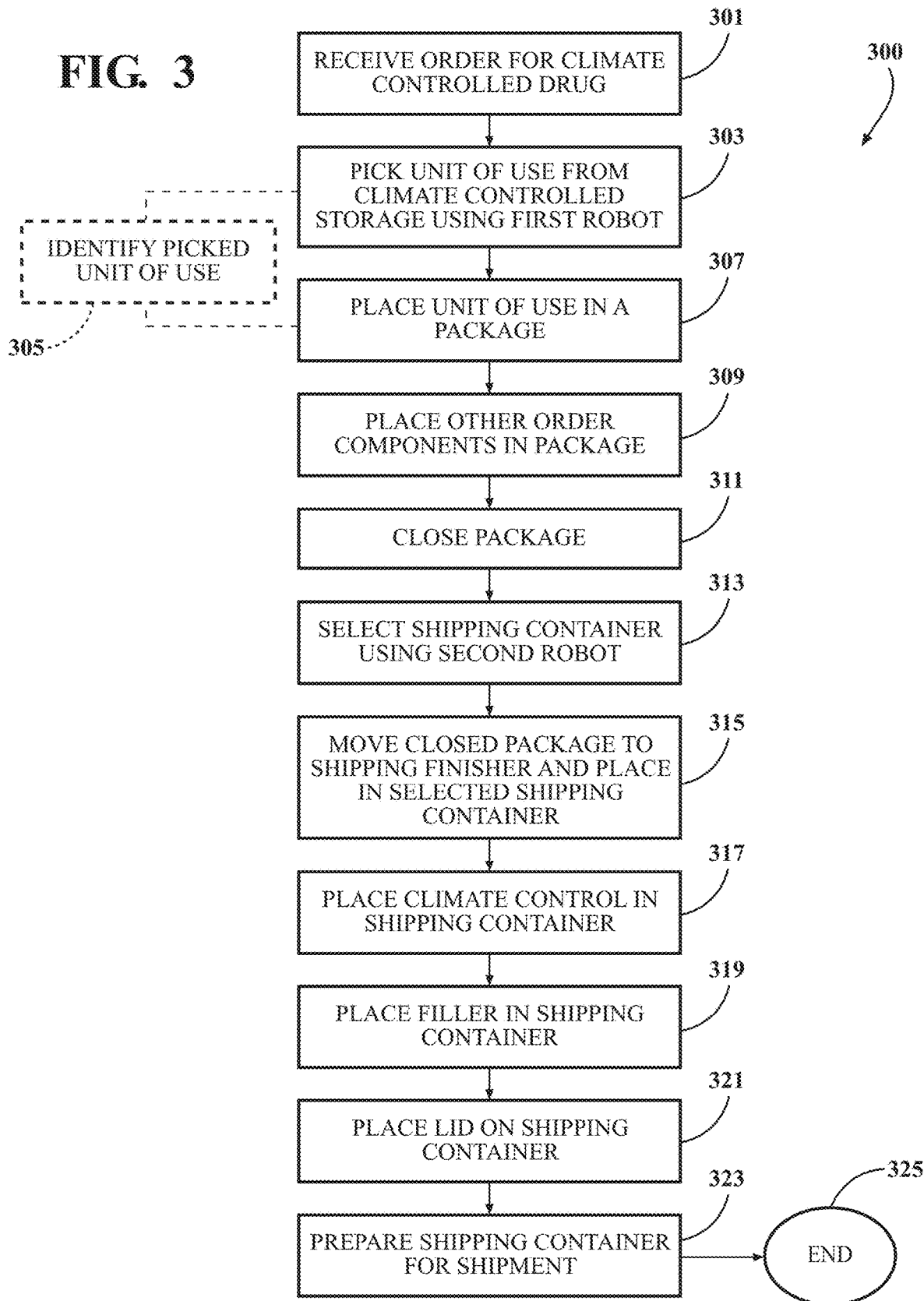

FIG. 6A
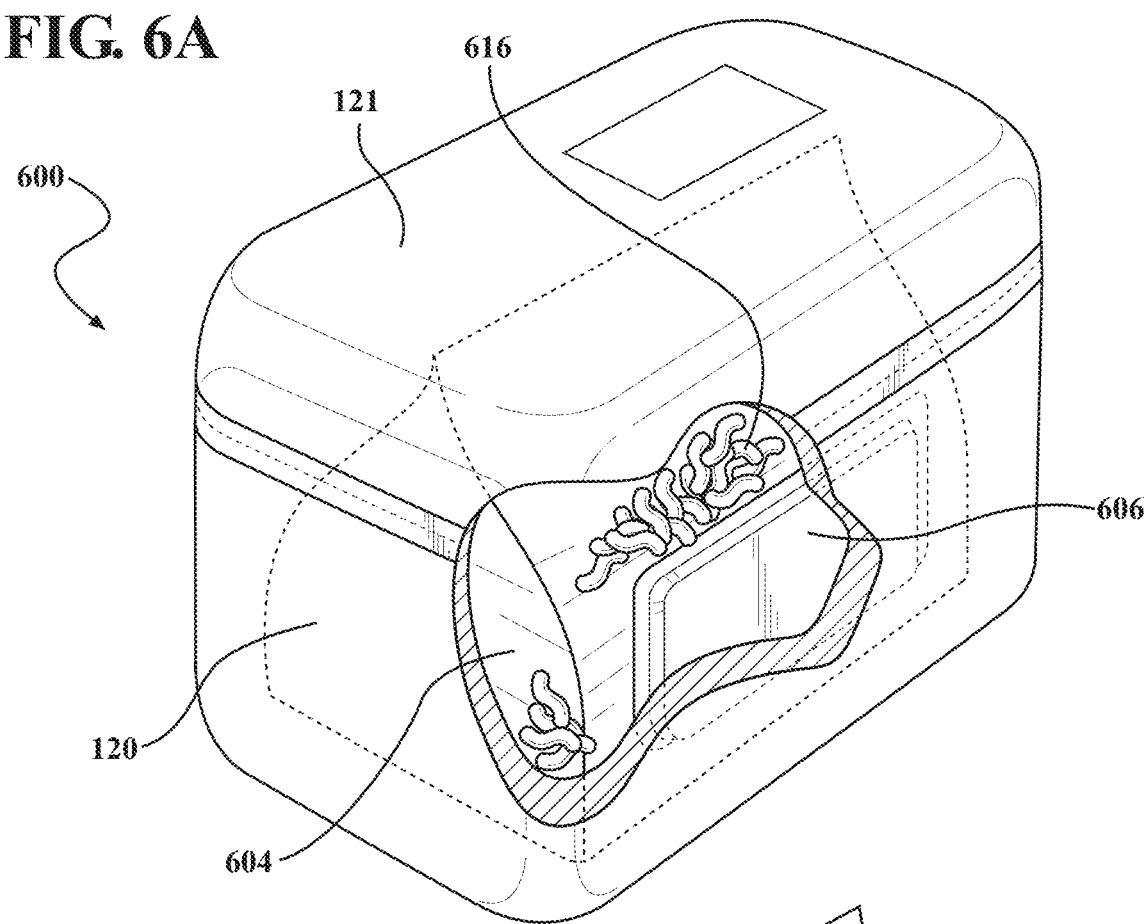
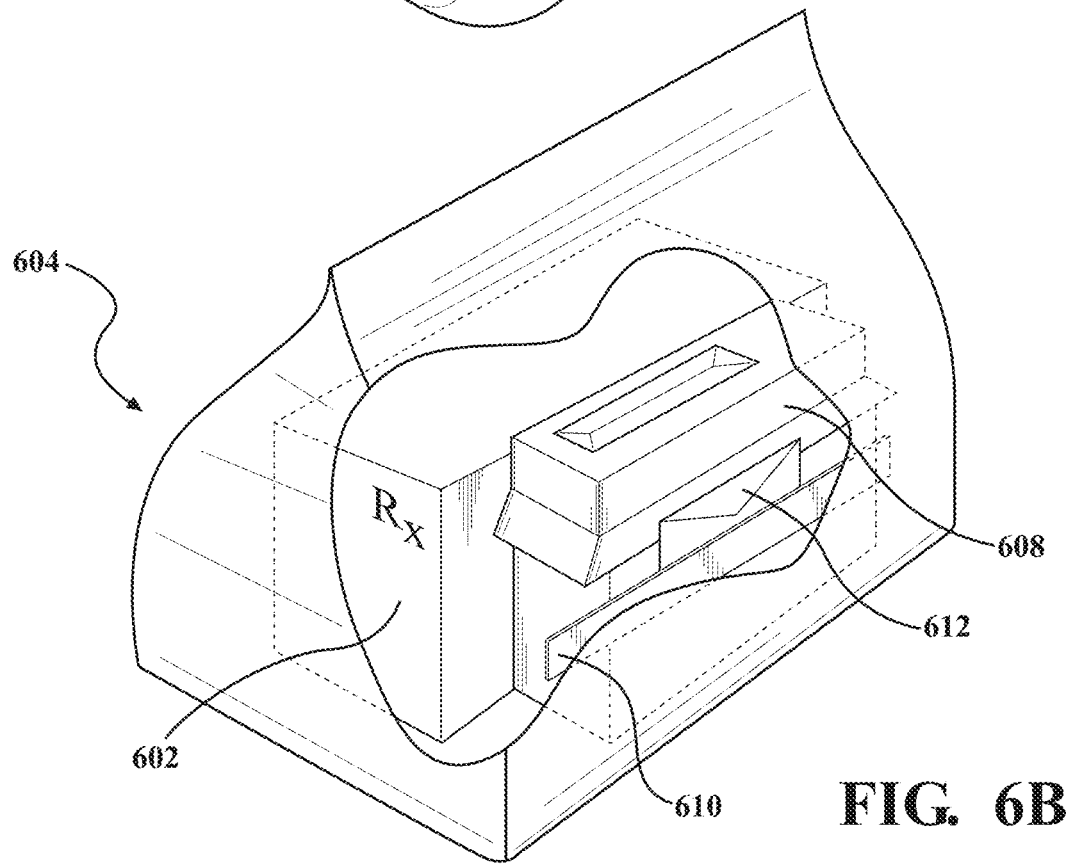
FIG. 6B

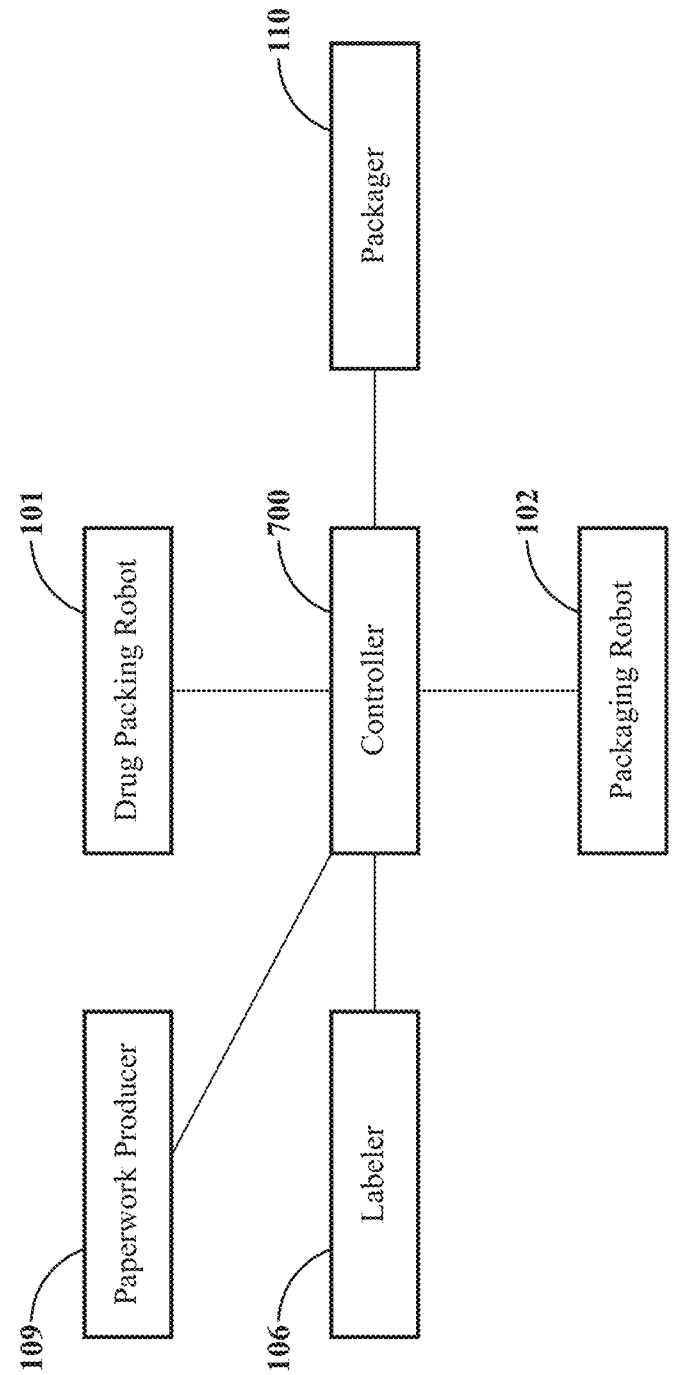

METHODS AND SYSTEMS FOR FILLING CLIMATE CONTROLLED MEDICATIONS

CROSS-REFERENCE TO RELATED APPLICATION

This Divisional application claims the benefit of U.S. Provisional Patent Application No. 62/910,837, filed on Oct. 4, 2019, entitled "METHODS AND SYSTEMS FOR FILLING CLIMATE CONTROLLED MEDICATIONS" and to U.S. patent application Ser. No. 17/062,266, filed on Oct. 2, 2020, entitled "METHODS AND SYSTEMS FOR FILLING CLIMATE CONTROLLED MEDICATIONS," the entire contents of which are hereby incorporated by reference.

FIELD

The present disclosure relates generally to the technical field of automated filling centers. In a specific example, the present disclosure can relate to a high-volume fulfillment center (e.g., a high-volume pharmacy, etc.) and to systems and methods for handling packaged units, which can include environmentally controlled packaged pharmaceuticals.

BACKGROUND

The background description provided here is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

An automated pharmacy can process and fill a large number of prescriptions and prescription orders. Automated systems can be used by a high-volume pharmacy to process and fulfill prescriptions.

Mail order pharmacies provide a convenient and cost-effective option for patients to receive prescription drugs. For example, a mail order pharmacy can be capable of taking advantage of economies of scale, volume dispensing of prescription drugs, and centralized warehousing and shipping to reduce the cost of prescription drugs purchased by patients of the mail order pharmacy. Some types of prescription drugs can have temperature-related storage and handling requirements in order to maintain the safety and efficacy of the drugs.

SUMMARY

An aspect of the present disclosure is related to a temperature-controlled medication packaging system that includes a storage with a temperature-controlled interior containing at least one medication. The packaging system further includes at least one shipping container and at least one coolant that is sized to fit within the at least one shipping container. A first robot is adapted to retrieve the at least one medication from the storage and transport the at least one medication to a second robot. The second robot is adapted to receive the at least one medication from the first robot and to bring the at least one medication and the at least one shipping container and the at least one coolant together for packaging.

In an embodiment, the second robot is adapted to place the at least one medication product and the at least one coolant inside of the at least one shipping container.

In an embodiment, a holding area is accessible by both of the first and second robots, the first robot is adapted to place the at least one medication in the holding area, and the second robot is adapted to retrieve the at least one medication from the holding area.

In an embodiment, the holding area is a packager that creates an intermediate package containing the at least one medication, and the second robot is adapted to place the intermediate package and the at least one coolant inside of the at least one shipping container.

In an embodiment, the at least one medication includes an environmentally sensitive medication and wherein the intermediate package further contains at least one of paperwork associated with the environmentally sensitive medication and a sharps container and a temperature and a temperature sensor.

In an embodiment, the second robot is further adapted to retrieve a lid and place the lid on the shipping container with the at least one medication and the at least one coolant contained therein.

In an embodiment, the at least one medication in the storage container includes a plurality of different types of medications, and the first robot is adapted to retrieve any of the different types of medications.

In an embodiment, the at least one coolant includes a plurality of different coolants having different cooling capabilities.

In an embodiment, the at least one shipping container includes a plurality of shipping containers having different sizes, and the second robot is adapted to retrieve any of the shipping containers of different sizes.

In an embodiment, the storage includes a plurality of tiers separated from one another by walls. Each tier extends from a first end that is distal from the first robot to a second end that is proximate the first robot.

In an embodiment, the tiers are angled downwardly from the respective first ends to the respective second ends.

In an embodiment, similar medications are disposed on each tier of the storage, and different medications are disposed on different tiers.

Another aspect of the present disclosure is related to a temperature-controlled medication packaging system including a storage with a temperature-controlled interior containing at least one medication. The packaging system further includes a temperature sensor supply including at least one temperature sensor. A first robot is adapted to retrieve the at least one medication and the at least one temperature sensor and to deliver them to a packager. The packager is adapted to produce an intermediate package containing the at least one medication and the at least one temperature sensor. The packaging system further includes at least one cooler supply including at least one cooler and at least one coolant supply including at least one coolant. A second robot is adapted to deliver the intermediate package, the at least one cooler, and the at least one coolant to a finisher.

In an embodiment, the at least one coolant includes at least two different coolants having different cooling capabilities, and the second robot is adapted to select one of the at least two coolants based at least the type of medication in the intermediate package and on a destination for the medication.

In an embodiment, the at least one cooler includes at least two differently sized coolers, and the second robot is adapted to select one of the at least two differently sized coolers based on the at least one medication in the intermediate package and based on a size of the selected one of the at least two different coolants.

Yet another aspect of the present disclosure is related to a method of producing a temperature-controlled medication package. The method includes the steps of, using a first robot, retrieving a medication from an environmentally controlled storage and delivering the medication to a holding area. The method proceeds with the steps of, using a second robot, retrieving the medication from the holding area and a shipping container and at least one coolant and delivering the medication, the shipping container, and the coolant to a finisher. The method continues with the step of packaging the medication and coolant into the shipping container.

In an embodiment, the holding area is a packager, and the method further includes the step of, at the packager, packaging the medication into an intermediate package.

In an embodiment, the method continues with the steps of, using the first robot, retrieving a temperature sensor and delivering the temperature sensor to the packager. The method then proceeds with the step of, at the packager, packaging the temperature sensor with the medication in the intermediate package.

In an embodiment, the method continues with the step of, using the first robot, retrieving at least one of a sharps container and paperwork and delivering the sharps container and/or paperwork to the packager. The method proceeds with the step of, at the packager, packaging at least one of the sharps container and the paperwork into the intermediate package.

In an embodiment, the method further includes the step of, with the second robot, inserting the intermediate package, the coolant, and a filler into the cooler and placing a lid on the cooler.

BRIEF DESCRIPTION OF THE DRAWINGS

The present disclosure will become more fully understood from the detailed description and the accompanying drawings.

FIG. 3 is an example process flow illustrating a method for filling a prescription order for an environmentally controlled drug in an automated pharmacy, according to an example embodiment.

FIG. 6A is a partial fragmentary view showing a shipping container of the type that may be produced by the systems of FIGS. 1 and 2;

FIG. 6B is a partial fragmentary view showing an intermediate package of the type that may be produced by the systems of FIGS. 1 and 2; and FIG. 7 is a schematic view showing an electrical system of the exemplary systems of FIGS. 1 and 2.

In the drawings, reference numbers can be reused to identify similar and/or identical elements.

DETAILED DESCRIPTION

Figure 1:
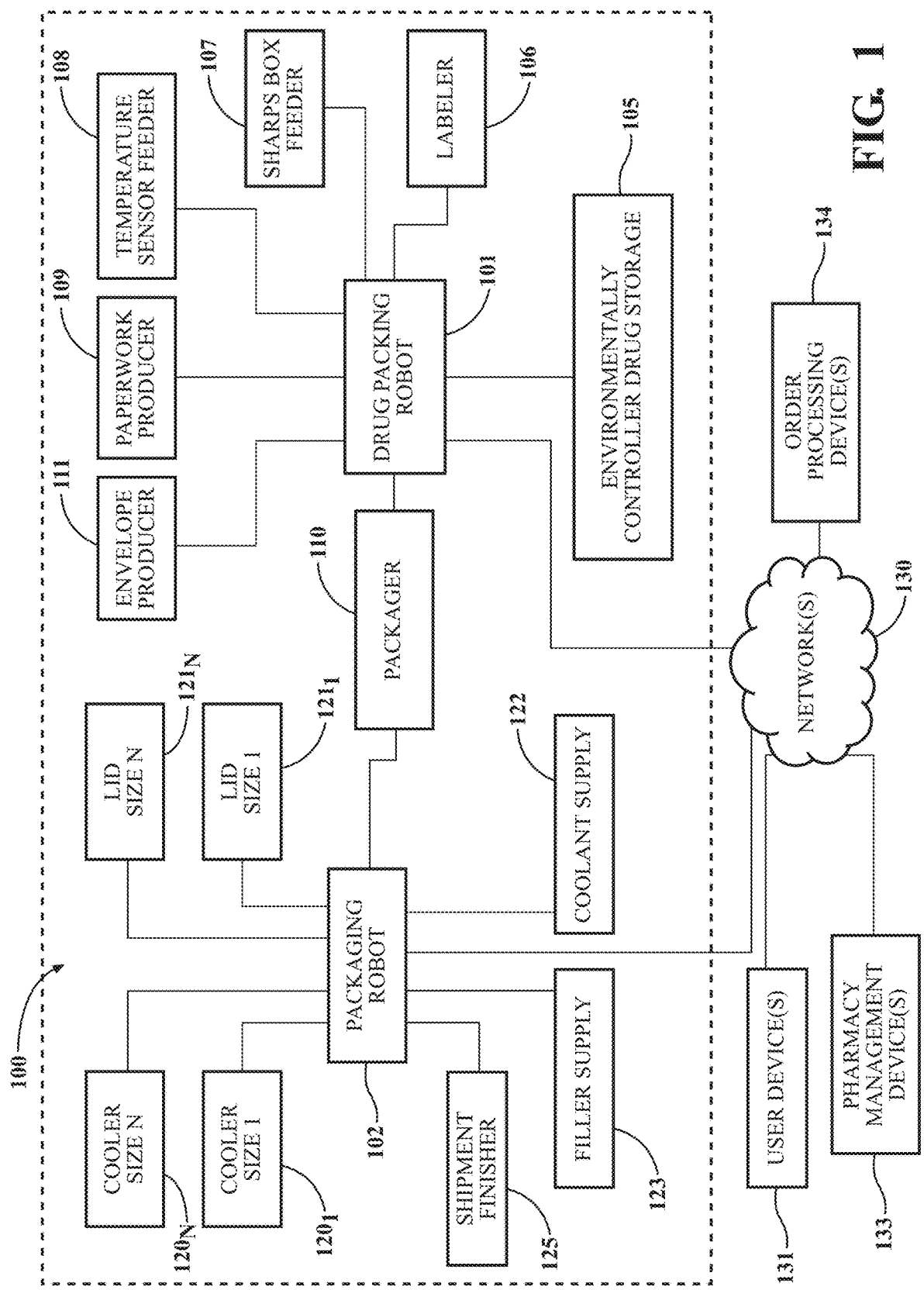
FIG. 1 is a diagram of an example implementation of a system for an automated pharmacy, according to an example embodiment.

Example systems and methods for filling drug orders including an environmentally controlled drug, for example, in an automated pharmacy, are described. In the following description, for purposes of explanation, numerous specific details are set forth in order to provide a thorough understanding of example embodiments. It will be evident, however, to one of ordinary skill in the art that these embodiments can be practiced without these specific details.

Generally, a prescription order is generated for an automated pharmacy, which can be a specialty pharmacy or a high-volume pharmacy. A high-volume pharmacy dispenses prescription drugs in a high volume. A high-volume pharmacy can include automatic pill dispensing systems to carry out the dispensing of the prescription drugs automatically at a rapid rate. A specialty pharmacy focuses on high cost, high touch medication therapy for patients with complex disease states. Medications in a specialty pharmacy range from oral to cutting edge injectable and biologic products. In each of these pharmacies, a drug can require environmental control while in storage and during shipping. The prescription order can include more than one prescription drug for fulfillment. Each prescription drug in a prescription order is an order component of the prescription order. Generally, the order components are pill bottles; liquid bottles; blister packs; unit-of-use packs or products; injectable packages; spray bottles; tubes; ampoules; drop counters; insulated boxes; child-resistant containers; or other packaging having a quantity of a prescription drug contained therein. At least one of the drugs in an order can require a controlled environment. An example of a controlled environment is one that maintains a required temperature range and/or humidity range. The controlled environment can be a lowered temperature. By way of example, certain insulin needs to be stored at a temperature less than room temperature, for example at less than 32 degrees Fahrenheit (32° F.).

The prescription drugs can be dispensed at various sections of the automated pharmacy, e.g., a high-volume pharmacy or a specialty pharmacy. Some prescription orders can require manual handling of certain order components. Some prescription order components can be filled automatically by filling machinery. It is one goal of the present disclosure to provide an automated system to fill prescription orders that include an environmentally controlled drug. The system can include at least two robots to retrieve, package, and prepare for shipping the prescription order with an environmentally controlled drug.

One example of a drug that requires temperature control is HUMIRA® (adalimumab), which can be supplied as a unit-of-use product, e.g., in prefilled syringes as a preservative-free, sterile solution for subcutaneous administration. There are various unit-of-use products or packages of Humira®. For example, one unit of use product of Humira® is a package containing a pen carton containing two alcohol preps, two dose trays, six alcohol preps, and six dose trays (or other numbers of dose trays). Each dose tray consists of a single-use pen, containing a 1 mL prefilled glass syringe with a fixed 27-gauge ½ inch needle, providing 40 mg (0.8 mL) of HUMIRA®. Like many drugs, HUMIRA® must be refrigerated, e.g., at 36° F. to 46° F. (2° C. to 8° C.) and not be frozen, e.g., a temperature above 32° F. (0° C.).

A drug that requires temperature control cannot be used if it falls outside of its exclusion time period. The exclusion time period is the time a drug can be outside of its environmental control and remain a useable drug. The exclusion time period can be a function of the time outside the environmental control and the magnitude of the change outside of the environmental control. In the case of a temperature-controlled drug, the exclusion time period can be function of time and the temperature difference between the controlled environment and the non-controlled environment. In the case of drugs, the pharmacist can set the exclusion time period. A temperature-controlled drug can have a storage temperature range for a specific time period, which can be zero seconds, less than one minute, less than two minutes, or less than five minutes. If a drug becomes frozen, then it typically cannot be thawed and used. When shipping or traveling with a temperature-controlled drug (for example, HUMIRA®) it must be stored in a shipping container that includes a cooler, which could be in the form of an ice pack or another thermally controlled carrier, to maintain the drug in the predetermined temperature range until the drug reaches its destination. Additionally, some drugs must be protected from direct sunlight, during storage and transport.

Another drug that requires environmental control is ENBREL®, which is stored between 36° F. and 46° F. (2° C. and 8° C.). This is the standard temperature for many home refrigerators. However, you can keep ENBREL® at room temperature (between 68° F. and 77° F., or 20° C. and 25° C.) for up to 14 days. Storing ENBREL® at room temperature in an automated pharmacy is not standard practice.

Other temperature-controlled drugs (including both prescription and over the counter drugs) can require different temperature ranges than ENBREL® or HUMIRA®, and the present disclosure is not limited just to these two exemplary medications. The present system can store the drugs at their required temperature ranges by storing the drugs, for example, in different cooler packages or in different zones of a single cooler package. The refrigerated cooler that stores the medication at the pharmacy also stores the medications in the required temperature ranges. It is within the scope of the present disclosure to store drugs and order components (such as sharps packages and instructions) and fill to orders with those drugs and order components along with a coolant to maintain the drugs in their required temperature ranges during shipping using the system and methods described herein.

FIG. 1 shows a diagram of an example implementation of an automated pharmacy system 100 for filling a shipping container including a temperature-controlled drug, and FIG. 6A shows an exemplary shipping package 600 produced by the system 100. The system 100 can be part of an automated pharmacy, e.g., a high-volume pharmacy. The system 100 uses multiple medication packing robots 101, 102 that can essentially access at least some distinct parts of the system 100 with at least one point or area or station where both robots 101, 102 have access. The robots 101, 102 can have respective individual arcs of movement to travel between multiple stations and move a medication or other objects related to a pharmaceutical order between the stations. A station can be a location at which a function is performed to complete an order, e.g., in the pharmacy. In an example embodiment, the robots 101, 102 can deliver a unit-of-use product 602 between stations. The robots 101, 102 can have six degrees of movement or more. The first robot 101 (hereinafter referred to as a "drug packing robot 101") can be mounted on a guide to move longitudinally in the pharmacy area for accessing additional stages or areas of stages beyond the reach of an arm of the drug packing robot 101. The drug packing robot 101 can have at least seven axes of movement. The drug packing robot 101 can be a unit-of-use robot that creates an intermediate package 604. The second robot 102 (hereinafter referred to as a "packaging robot 102") operates to take the intermediate package 604 and create the shipping package 600 including the intermediate package 604 in addition to environmental controls 606 that are able to hold the unit-of-use product 602 in a required environment until it is delivered to a customer.

The robots 101, 102 each include end of arm tooling adapted to engage the unit-of-use product 602 through, for example, grasping, suction, etc. The end of arm tooling includes various bag and box gripping solutions for various packaging such as bags, blister packs, boxes, bottles, ampules, syringes, medication containers and the like. The robots 101, 102 can each include one or more end of arm tools. By way of example, a first end of arm tool is adapted to engage a unit-of-use product 602, a second end of arm tool is adapted to engage a sharps box, a third end of arm tool is adapted to engage a shipping box, a fourth end of arm tool is adapted to engage a lid for the shipping, a fifth end of arm tool is adapted to engage a bag containing the unit-of-use product 602, and a sixth end of arm tool is adapted to engage paperwork. The robots 101, 102 can be adapted to physically interact with humans in a shared workspace and can be 6 or 7-axis robots.

An environmentally controlled storage 105 holds at least one type of drug at its required environment. The storage 105 can be a refrigerated cooler that has an internal temperature within the temperature range for each medication type stored therein, e.g., between 36-40° F. (2-8° C.). When multiple medication types having different storage temperature ranges are stored, the storage 105 can have different zones that maintain different temperatures. The storage 105 can include a first, long-term storage area and a second, reach-in storage area. The first storage area can be an enclosed, insulated room that is accessible through a latchable door in the room defined by insulated walls, floor and ceiling. A refrigeration unit keeps the room at a set temperature using a temperature controller. The second storage area can have an open side through which the drug packaging robot 101 can retrieve a unit-of-use product 602 of a prescribed medication or other drug. The second storage area can have movable conveyors therein to move a certain unit-of-use product 602 to the open side of the storage 105 so that it is graspable by the drug packaging robot 101. The second storage area can include a second refrigeration unit to keep the second storage area at a set temperature using a temperature controller. The second storage area can include a curtain at its open side to reduce the temperature loss through the open side. The drug packing robot 101 can reach through the curtain to pick the medication or drug from the second storage area.

The storage 105 can include multiple platforms to hold the unit-of-use products 602 above the floor. By way of example, the platforms can be slides that have an entry end at which unit-of-use products 602 are inserted and an exit end at which the drug packing robot 101 can remove a unit-of-use product 602. In an example embodiment, the entry end is higher than the exit end. Thus, the unit-of-use products 602 on a platform can slide toward the exit end due to gravity. The platforms can also include rollers that reduce the friction on the slide so that the unit-of-use products 602 more easily fall toward the exit end. In some embodiments, a spring-loaded pusher can located be at the rear of the unit-of-use product 602 on any individual platform to urge the unit-of-use product 602 to the exit end. The side of the storage 105 where the exit end is positioned can be open to allow the drug packing robot 101 access to the unit-of-use products 602 at the exit end. The platforms can include conveyors that are at least partially positioned in the long-term storage area so that the conveyor can move a selected unit-of-use product 602 to a location that is reachable by the drug packing robot 101. The conveyors include a moveable surface that is moved by a motor under direction of a controller to position a unit-of-use product 602. The storage 105 can vent chilled air at the exit end to form a temperature curtain at the exit end. The other sides of the storage 105 can be enclosed to maximize the efficiency of the refrigeration unit. The side of the storage 105 with the entry end can include moveable doors to selectively enclose that side of the storage 105 while allowing access to load the storage 105 with unit-of-use products 602 when open and reduce thermal conductivity and efficiency losses when closed. The platforms can include sensors that sense the level of unit-of-use product 602 on each slide and report inventory in the cooler to a central processor.

A labeler 106 is positioned in the arc of movement of the drug packing robot 101. The labeler 106 can print a label with prescription data and adhere the label to a selected unit-of-use product 602 with the assistance of the drug packing robot 101.

A sharps box feeder 107 is positioned in the arc of movement of the drug packing robot 101. The sharps box feeder 107 provides a sharps box 608 to the drug packing robot 101 and for placement into the intermediate package 604 with the unit-of-use product 602. The drug packing robot 101 will select a sharps box 608, if required by the order, from the sharps box feeder 107. In an example embodiment, the sharps box 608 will be retrieved by the same end of arm tool of the drug packing robot 101 as that retrieves the unit-of-use product 602. In another embodiment, the drug packing robot 101 can include a first end of arm tool to engage the unit-of-use product 602 and a different second end of arm tool to engage the sharps box 608.

A temperature sensor feeder 108 is positioned in the arc of movement of the drug packing robot 101. The temperature sensor feeder 108 provides a sensor 610 that can be packaged in the intermediate package 604 with the unit-of-use product 602. The sensor 610 will be retrieved by the same end of arm tool of the drug packing robot 101 that retrieves the unit-of-use product 602 or a different end of arm tool. In another embodiment, the temperature sensor 610 can be placed directly in the shipping package 600 rather than in the intermediate package 604. In some embodiments, the temperature sensor 610 may not be included in the shipping package 600. The controller 700 (shown in FIG. 7) will track those unit-of-use products 602 that require the temperature sensor 610 and, if required, will instruct the drug packing robot 101 to retrieve the temperature sensor 610 from the temperatures sensor feeder 108 and place it in the intermediate package 604 but not for other prescriptions when not required. In one embodiment, the temperature sensor feeder 108 can include a plurality of different types of temperatures sensors 610, which are adapted for use with different types of medications that have different temperature range and time requirements.

A paperwork producer 109 is positioned in the arc of movement of the drug packing robot 101. The paperwork producer 109 provides paperwork to be packages with the unit-of-use product 610. The paperwork can be retrieved by the same arm of the drug packing robot 101 that retrieves the unit-of-use product 602 in an example embodiment. The paperwork may include, for example, drug information and/or dosage instructions.

An envelope feeder 111 is positioned in the arc of movement of the drug packing robot 101. The envelope feeder 111 provides an envelope 612 in which the paperwork is stored. The envelope 612 can be packaged with the unit-of-use product 602 in the intermediate package 604. The envelope 612 can be retrieved by the same end of arm tool of the drug packing robot 101 that retrieves the unit-of-use product 602 in an example embodiment or a different end of arm tool. The envelope feeder 111 and the paperwork producer 109 can be part of a single paperwork system to produce the paperwork. For example, in one embodiment, the envelope feeder 111 can feed an envelope to the paperwork producer 109, which folds the paperwork together places it in an empty envelope 612 and feeds the assembled envelope 612 containing the paperwork to the drug packing robot 101.

A packager 110 is positioned in the arc of movement of the drug packing robot 101. The packager 110 can be a top load bagger that creates a sealed bag as the intermediate package 604 containing the unit-of-use product 602 and other components (for example, a sharps box 608, a temperature sensor 610, and/or an envelope 612 containing paperwork) of the order. In some embodiments, the intermediate package 604 is a sealable bag that can be sealed by a thermally activated seal or a mechanical seal formed between two opposed edges of the bag. In an example embodiment, the intermediate package 604 includes an adhesive on at least one side that adheres the two sides of the opening together to close the opening in the sealed bag.

The packaging robot 102 is positioned such that the packager 110 is within its arc of movement so that the packaging robot 102 can reach the intermediate package 604 placed on the packager 110 by the drug packing robot 101. The packaging robot 102 is designed to be able to grip and move the package and other shipping components. As discussed in further detail below, the packaging robot 102 selects a shipping package from multiple possible packages, e.g., differently sized packages that are insulated shipping coolers.

Cooler supplies are positioned in the arc of movement of the packaging robot 102. The cooler supplies can store different sizes of shipping coolers $120_1 \ldots 120_N$ and different sizes of lids $121_1 \ldots 121_N$ that correspond to the different cooler sizes. In operation, the controller 700 instructs the packaging robot 102 to select the appropriately sized shipping cooler $120_1 \ldots 120_N$ for the order and move the selected cooler 120 to the shipment finisher 125. The shipping cooler 120 can be selected based on the size of the intermediate package 604 plus the size of the coolant 606 required to maintain the medication of the unit-of-use product 602 in its safe temperature range until the shipping package 600 reaches its destination. The packaging robot 102 also retrieves the appropriate lid $121_1 \ldots 121_N$ based on the selected cooler and delivers the selected lid to the shipment finisher 125.

A coolant supply 122 is positioned in the arc of movement of the packaging robot 102 and includes coolants 606 (for example, ice packs or gel packs or any suitable means for controlling temperature in the shipping package 600) to the packaging robot 102 for inclusion in the shipping package 600. The packaging robot 102 can select the size or amount of coolant to be placed with the order package in selected shipping cooler, e.g., at the shipment finisher 125. The coolant supply 122 may include different types and/or quantities of coolants 606 that have different cooling capabilities. For example, the coolants 606 may be able to maintain the contents of the shipping package 600 at different temperatures and for different periods of time based on, for example, the type of unit-of-use product 602 and its intended destination.

A filler supply 123 is positioned in the arc of movement of the packaging robot 102 for supplying a filling material 616 to the packaging robot 102. The controller directs the packaging robot 102 to select the appropriate size and/or amount of filling material 616 to be placed with the intermediate package 604 and the coolant 606 in the shipping cooler 120, e.g., at the shipment finisher 125. The filling material 616 can be, for example, air bags, bubble wrap, packing peanuts, or the like.

In operation, the shipment finisher 125 receives all of the shipment components from the packaging robot 102 and either itself (with, for example, an additional robot) places those components into the cooler 120 or allows the packaging robot 102 to place those components into the cooler 120. Thereafter, either the packaging robot 102 or the shipment finisher 125 places the lid 121 on the cooler 120. The shipment finisher 125 can tape shut the shipping cooler 120 and apply a shipping label to create the shipping package 600. The finisher 125 can also shrink wrap the cooler 120.

A communication network 130 can provide instructions to the robots 101, 102 to fill a prescription order requiring a climate-controlled drug, which can be stored in the environmentally controlled drug storage 105. A user device 131 can submit a prescription order through the network 130. The user device 131 can include encryption to safeguard the prescription data. A pharmacy management device 133 is in communication through the network 130 and can receive the prescription. The pharmacy management device 133 can adjudicate the prescription claim and, if an automated pharmacy flag exists in the records associated with the patient, stored in electronic memory, the device 133 can instruct an order processing device 134, e.g., through the network 130, to fill the prescription at an automated pharmacy, e.g., pharmacy 100. The order processing device 134 can track the types of drugs that are stored in the climate-controlled storage 105 and if in the storage 105 and part of the prescription, instruct the robots 101, 102 to fill and package the climate-controlled drug as part of the prescription order.

Figure 2:
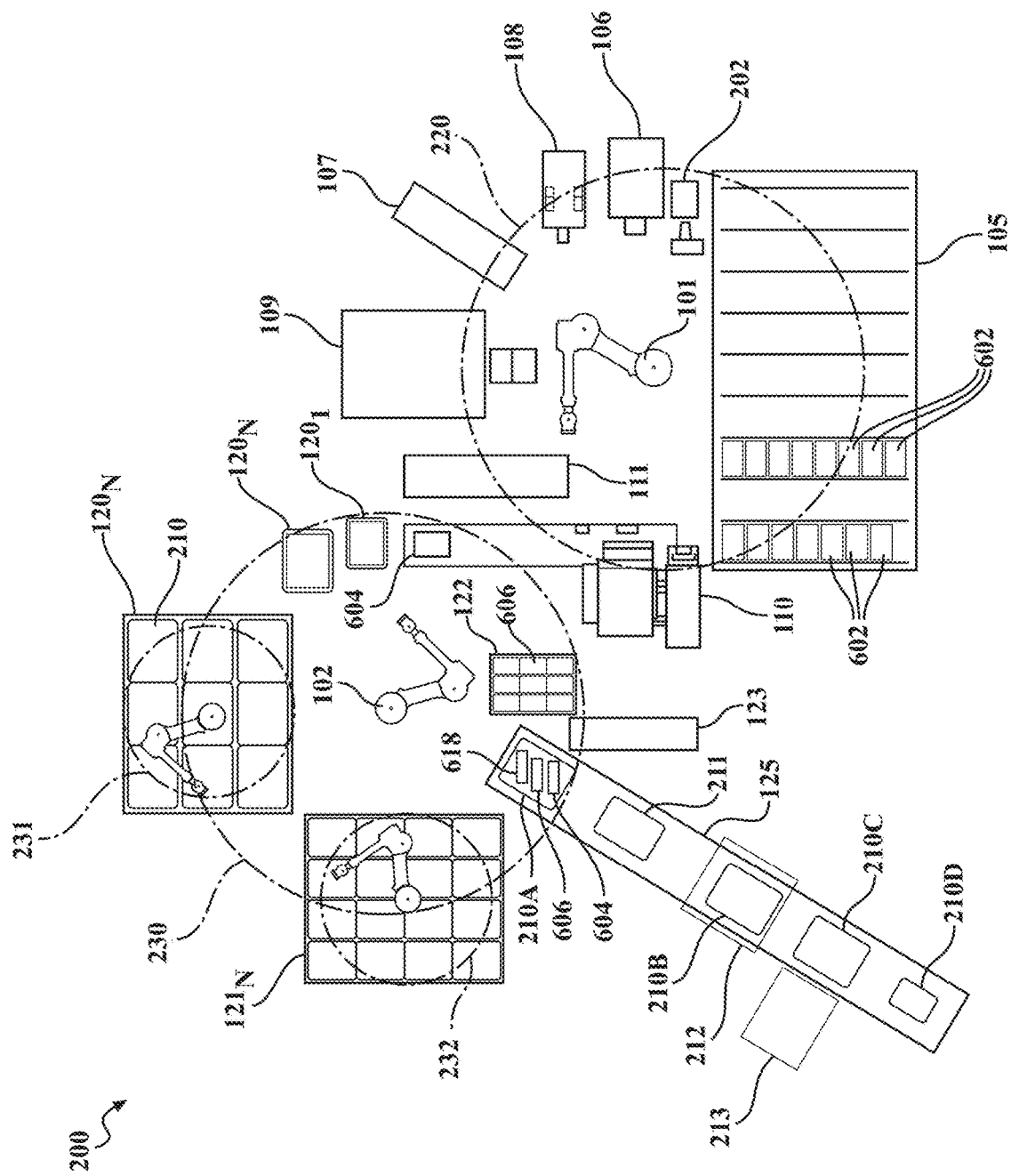
FIG. 2 is a diagram of an example implementation of a system for an automated pharmacy, according to an example embodiment.

FIG. 2 shows a diagram of an example implementation of an automated pharmacy system 200, according to an example embodiment. Elements shown in FIG. 2 that are the same as those shown in FIG. 1 are designated with the same reference number. Additional elements are designated with a new number with the most significant digit being a "2".

A code reader 202 is provided in the arc of movement 220 of the drug packing robot 101. The code reader 202 can include a camera or a laser reader and processor to recognize an image from the camera or to convert reflected light from a unit-of-use product 602 into a digital code to be stored in memory and compared to a record in memory. The code reader can be a bar code reader, an alphanumeric reader, a quick-read (QR) reader, or the like. The drug packing robot 101 can move an engaged unit-of-use product 602 to the code reader 202 to confirm the correct unit-of-use product 602 is selected and compare the selected unit-of-use product 602 to the prescription order prior to placing the unit-of-use product 602 in the intermediate package 604.

The drug packing robot 101 has an arc of movement 220 that extends to, and over at least portions of, the stations 106-111 and 202, at which various functions to package orders, which can include environmentally controlled components are prepared.

The sealed intermediate sealed package 604, including the unit-of-use product 602 that is processed by the drug packing robot 101, is stored at the packager 110 within the arcs of movement 220, 230 of the drug packing robot 101 and the packaging robot 102 respectively. In use, the packager 110 can function as a holding area for holding one or more intermediate packages 604 awaiting processing by the packaging robot 102. The packager 110 may include a conveyor for moving intermediate packages 604 from one area that overlaps with only the arc of movement of the drug packing robot 101 to an area that overlaps only with the arc of movement of the packaging robot 102. On this conveyor, multiple intermediate sealed packages 604 can be queued for processing by the packaging robot 102.

The cooler supply $120_1$ stores a small size cooler 211 relative to the cooler supply $120_N$, which stores a larger size cooler 210. The supplies $120_1, \ldots, 120_N$ are at least partially within the arc of movement 230. The packaging robot 102 can have a second arm with a further arc of movement 231, 232 to allow the selection of a cooler 210 or 211. In other words, the packaging robot 102 may include multiple robotic arms, which operate independently of one another to allow the packaging robot 102 to reach further distances than would be possible with only a single robotic arm.

The shipment finisher 125 includes various locations with at least one being within the arc of movement 230 of the packaging robot 102. In operation, a selected large cooler 210A is positioned at the beginning location at the shipment finisher 125. The packaging robot 102 places the intermediate package 604, which includes the intermediate package 604, the coolant 606, and the filling material 618 in the cooler 210A. The shipment finisher 125 can include a conveyor belt to move the closed, loaded cooler to additional locations. A closed small cooler 211, which includes a unit-of-use product 602 therein, is supported on the conveyor of the finisher 125. A cooler 210B is positioned in a finisher 212. The finisher 212 can be a taping device, a wrap seal device, or other device to secure the cooler 210B for shipment. A shipment labeler 213 is downstream of the finisher 212 and applies a shipping label to the outside of the cooler 210C. Cooler 210D has been labeled and sealed and holds the unit-of-use product 602 therein. The cooler 210D can be then picked up by the mail carrier of shipping company for delivery to the patient. The finisher 212 can alternately deliver an unlabeled but filled cooler 210 to an accumulation station 430 (shown in FIG. 4B and discussed in further detail below) for packaging with other, non-environmentally sensitive drugs or products.

The drug packing robot 101 operates to feed components to create a sealed intermediate package 604 including the unit-of-use product 602, a sharps box 608 (if needed), a temperature sensor 610, and paperwork (e.g., dosage information) associated with the prescription. The packager 110 seals these drug order components into the intermediate package 604. The packager 110 can also operate to reduce or expel air from the intermediate package 604 prior to sealing the intermediate package 604. The packaging robot 102 then has access to the intermediate package 604. The packaging robot 102 picks the appropriate cooler 210 and quality of coolant 614 for the intermediate package 604 based on the type of unit-of-use product 602 and the destination and assembles these components for shipping.

The system 100 can all be contained within a temperature-controlled environment. The entire system 100 can be maintained at the required temperature for the unit-of-use product 602, which cannot be a temperature at which a person can work for any significant period of time.

The system 100 selects the appropriate cooler 210, 211 and amount of coolant 207 plus any packaging filler 209 in the cooler. The amount and/or type of coolant 614 (for example, one or more gel or ice packs) is selected to ensure the unit-of-use product 602 is maintained with in the temperature range until it reaches its final destination. This can be done using the systems and methods described in U.S. patent application Ser. No. 14/630,373, titled Methods and Systems for Prescription Drug Shipping Selection, filed 24 Feb. 2015, which is incorporated by reference herein. Additional methods and systems for using ice or other coolant are described in U.S. patent application Ser. No. 11/818,330, titled Containers for Transferring Products and Methods for Their Transfer, filed 14 Jun. 2007, is hereby incorporated by reference.

FIG. 3 is an example process flow illustrating a method 300 for filling a prescription order including an environmentally controlled drug in an automated pharmacy, according to an example embodiment. In various example embodiments, the systems 100, 200 can execute the method 300 or parts of method 300.

At block 301, an order for a drug that is climate controlled is received, e.g., at a controller or control circuitry at an order fulfillment center. The drug is a unit-of-use product 602. At block 303, the unit-of-use product 602 is picked from the climate-controlled storage 105 by a first robot, e.g., the drug packing robot 101. At block 305, in some embodiments, the picked unit-of-use product 602 is identified, e.g., by the first robot moving the unit-of-use product 602 to a code reader 202 (such as a laser reader). At block 307, the picked unit-of-use product 602 is placed in an intermediate package 604. At block 309, other components (for example, an envelope 612 containing paperwork, a sharps box 608, a temperature sensor 610, etc.) are placed in the intermediate package 604. The preceding steps that require movement of material can be performed by the drug packing robot 101.

At block 311, the intermediate package 604, containing the unit-of-use product 602 and other components, is closed by the packager 110. At block 313, a shipping container (such as a cooler 120) is selected for the closed package.

At block 315, the cooler 120 is moved to a shipping finisher 125 and the intermediate package 602 is placed in the cooler 120 by a second robot, e.g., the packaging robot 102. At block 317, a climate control (such as the coolant 606), as needed, is placed in the cooler 120. The coolant 606 can be, for example, a cooling gel or an ice pack. The type of coolant 606 is selected using the controller 700 (shown in FIG. 7) based on factors, such as outside temperatures, distance to delivery, type of delivery, shipment method, type of shipment package, and the like. At block 319, the filling material 618 is placed in the cooler 120, as needed. At block 321, a lid 121 is placed on the cooler 120. The steps 315-321 can be at least partially performed by the packaging robot 102 to create a shipping package 600.

At block 323, the shipping package 600 is prepared for shipping, e.g., tape or shrink wrap, then label for the mail carrier or shipping company. At block 325, the process ends. Ending results in a single prescription being packaged and shipped to a customer. The process steps can be performed in the order described above, another order, or performed simultaneously for different prescriptions. For example, the drug packing robot 101 can be picking a unit-of-use product 602 from the storage 105 while the packaging robot 102 is preparing a sealed package for a different order. The end can also signal to the controller 700 that the system 100 is awaiting a further prescription to fill.

Figure 4A:
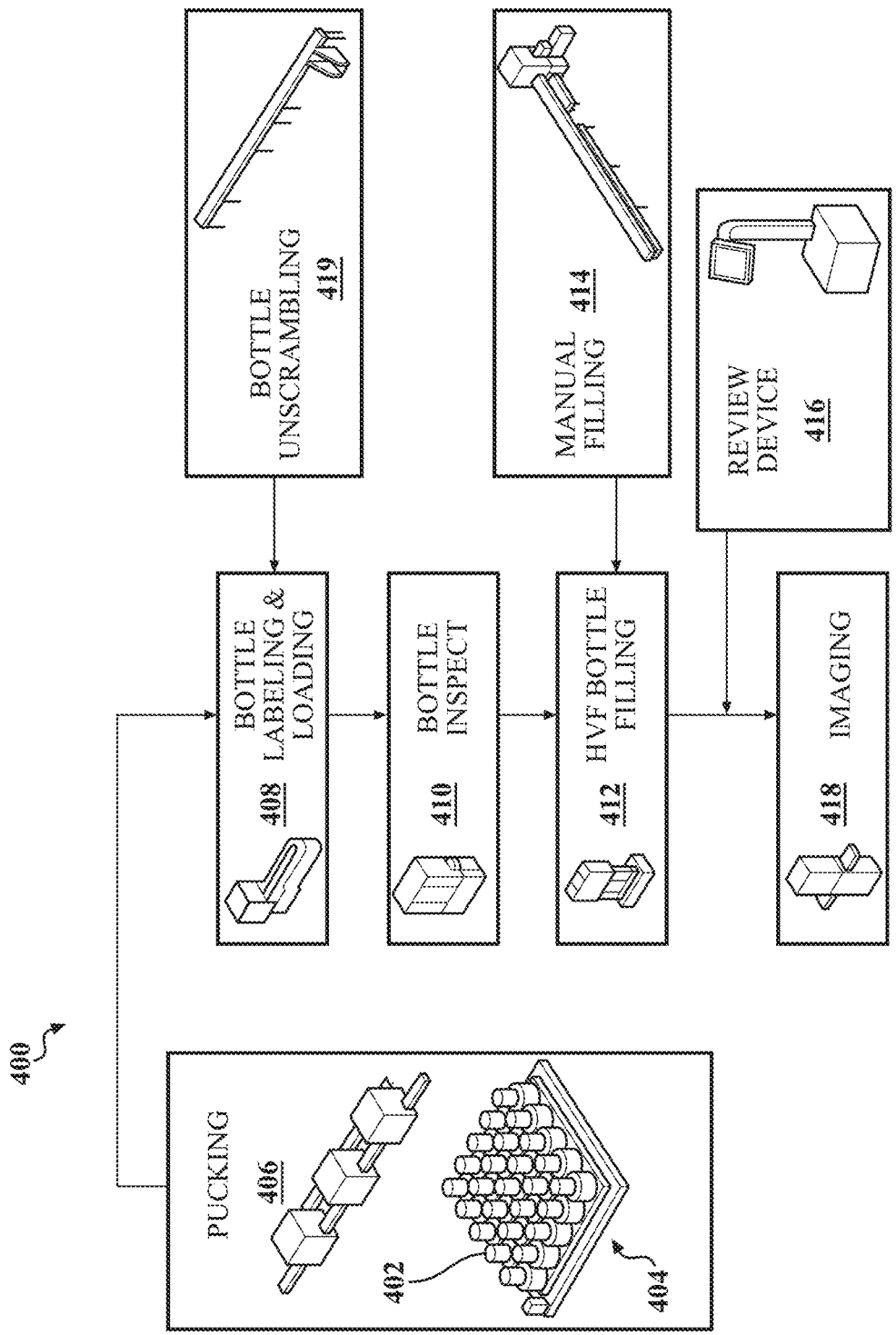
FIG. 4A is a diagram of an example implementation of a system for an automated pharmacy, according to an example embodiment.

FIG. 4A is a diagram of an example implementation of a system for an automated pharmacy, according to an example embodiment.

Figure 4B:
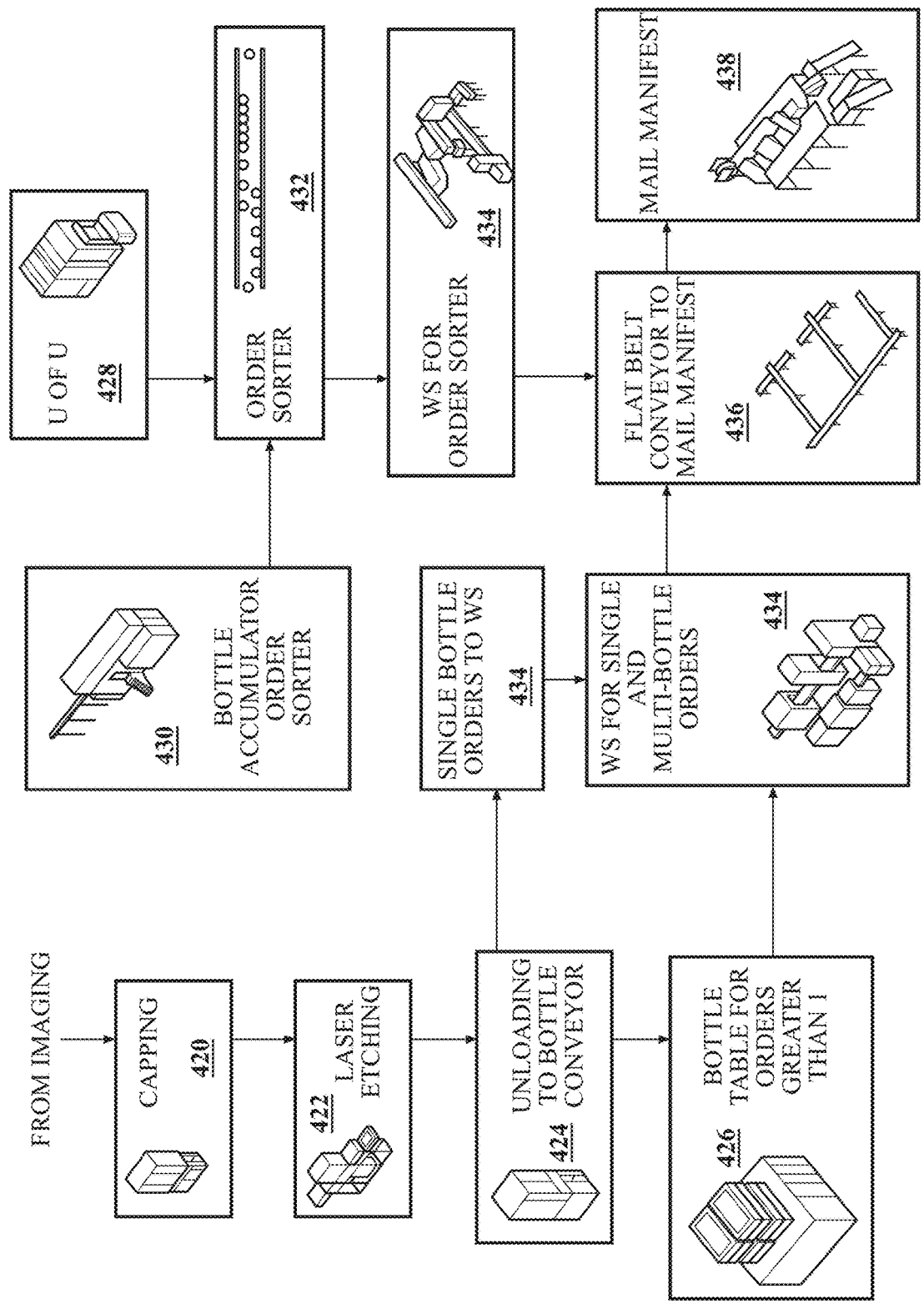
FIG. 4B is a diagram of an example implementation of a system for an automated pharmacy, according to an example embodiment.

In an automated or high-volume pharmacy (HVP) system generally designated 400 and shown in FIGS. 4A and 4B, an order is generated that can include one or more components including, for example, prescription drugs and/or supplements (generally product), for fulfillment. Generally, the order components include containers, unit-of-use products, or other packaging having a quantity of a prescription drugs, supplements, or the like therein. The unit-of-use products can be environmentally controlled, e.g., stored in cooler. The components of a given order can be separated in time and space within the system 400 and are therefore routed to various holding areas and processing areas within the system 400 so that all of the order components of an order can be joined together, or "married", for packing and further processing. The system 400 can include the system 100 (shown in FIG. 1) to handle environmentally controlled components of an order. The system 400 can join the enclosed shipment package 600 (shown in FIG. 6A) with other order components in an example. In another example, the components of an order can be processed separately but arrive at the outgoing shipment from the pharmacy at the same time or ready for delivery to the carrier at the same time.

Note that the pharmacy described herein is an automated pharmacy, e.g., a high-volume pharmacy, in contrast with a retail pharmacy or a specialty pharmacy, for example. While the system 100 is described as being deployed in a high-volume fulfillment center (e.g., a mail order pharmacy, a direct delivery pharmacy, and the like), the system 100 and/or components thereof can be deployed in a retail pharmacy or a specialty pharmacy, for example.

Pucking

The system 400 transports containers 402 (e.g., between devices described in the system 400) by use of pallets 404. A pallet sizing and pucking device 406 configures pucks in a pallet. The term "puck" is meant to describe a receptacle sized shaped and configured to receive a specific container 402. There can be many different sizes of containers and a corresponding puck can be needed to hold the container in the pallet receptacle. A puck is placed in a cavity in a pallet 404 by the pallet sizing and pucking device 406. Containers 402 are supported by the pucks during carriage in the pallet 404. Different pucks can have differently sized and shaped receptacles to accommodate containers 402 of differing sizes and shapes. The pallet 104 defines a transport structure for a number of pucks and the containers 102. The pallet 104 can include a number of cavities that each receive a puck and/or a container 102.

In some example embodiments, the pallet includes receptacles sized to receive the containers and need not include pucks to size the pallet receptacles to receive the containers 402. The use of a single container can allow for pallets to have receptacles sized for the single size container 402.

Bottle Loading and Labeling

The automated pharmacy system 400 also includes a loading device 408 for loading containers 402 into the pucks on a pallet 404 by for example, a robotic arm, pick and place mechanism, or other suitable device. The loading device 408 can also print a label (not shown) appropriate for a container 402, which is to be loaded onto the pallet 404, and apply the label to the container 402. The pallet 404 can be located on a conveyor assembly during these operations, e.g., at the automated pharmacy system 400.

Unscramble Device

A container unscrambling device 419 of the pharmacy system 400 is used to take a container of empty containers 402 either from a box, a bin, or other container, and orient the containers 402 in the correct position and load the containers 402 onto the infeed conveyors for further processing within the system 400.

Bottle Inspect

The pharmacy system 400 also includes a bottle inspect device 410 configured to verify, among other functions, that containers 402 in pallet 404 are correctly labeled and in the correct position on the pallet 404. The inspect device 410 suitably scans a label (barcode, text, or other suitable image) on container 402 on the pallet 404. Labels of the containers 402 can be scanned or imaged in full or in part by the inspect device 410. Such imaging can occur after container 402 has been lifted out of its puck by a robotic arm, picker, or the like, or can be otherwise scanned or imaged while retained in the puck. In some embodiments, images and/or video captured by the inspect device 410 can be stored in a storage device as order data.

Auto HVF Filling

An automated high-volume fill (HVF) bottle filling device 412 dispenses ordered medications or similar things into containers 402 in accordance with associated orders. HVF bottle filling device 412 includes high volume fillers that fill a number of drug types at a rapid rate. High volume fillers store a significant quantity of medication units, e.g., pills, tablets, gel caps, capsules, and the like, and count and dispense an ordered quantity into a container assigned to an order. The device 412 can be automated. Orders dispensed by the HVF bottle filling devices 412 can be packaged individually or in a container for shipping or can be shipped in combination with other orders dispensed by other devices in the pharmacy system 400. The other orders can be the environmentally controlled orders as described herein. Within the HVF bottle filling device 412 are secondary staging devices (not shown) that allow the orders to be pre-staged per order prior to the container 402 actually arriving at the dispense position or lane/area.

Manual Filling

A manual fulfillment station 414 is configured for manual fulfillment of orders. For example, manual fulfillment station 414 is configured to enable fulfillment of drugs in the container 402 by a pharmacist or pharmacy technician. In some embodiments, manual fulfillment station 414 provides the filled container 402 to another device in the pharmacy system 400 to be joined with other containers 402 in an order for a patient or member.

Orders dispensed by manual fulfillment station 414 are packaged individually or collectively for shipping. The order component from the manual fulfillment station 414 can be shipped in combination with other products dispensed by other devices in the pharmacy system 400, e.g., an environmentally controlled order component from system 100.

In general, manual fulfillment includes operations at least partially performed by a pharmacist and/or pharmacy technician. For example, manual order filler at the station 414 retrieves a supply of a prescription drug, makes an observation, counts out a prescribed quantity of drugs and places them into container 402, or the like with at least part of this operation being manual. Some portions of the manual fulfillment process can be automated by use of a machine. For example, counting of capsules, tablets, or pills can be at least partially automated (e.g., through use of a pill counter). The manual fulfillment station 414 also includes multiple devices (not shown) that capture an image of the medications and/or weighs the medications to aid the pharmacist or technician in counting and verifying that the correct count has been reached.

Review Device

A review device 416 processes containers 402 to be reviewed by a pharmacist for proper pill count, exception handling, verification, and the like. Fulfilled prescriptions reviewed and/or verified by a pharmacist, as can be required by state or local law, either manually or using a review device 416. A pharmacist dispenses certain drugs in compliance with local and/or other laws and operates the review device 416 to visually inspect a container 402 that has been filled with a prescription drug. The pharmacist reviews, verifies, and/or evaluates drug quantity, drug strength, and/or drug interaction concerns, or otherwise performs pharmacist services. The pharmacist also handles containers 402 that have been flagged as an exception, such as containers 402 with unreadable labels, containers 102 for which the associated order has been cancelled, containers 402 with defects, and the like.

Imaging

The pharmacy system 400 also includes an imaging station 418 that includes an imager (for example, a camera), which can image containers 402 after they have been filled with product, e.g., a medication. The imaging station 418 measures the fill height of the product in the container 402 based on the obtained image to determine if the container 402 is filled to the correct height given the type of product and the number of pills in the prescription. Images of the pills in the container 402 can also be obtained to detect the size of the pills themselves and markings thereon. The images can be transmitted to the order processing device 400, and/or stored in the storage device 402 as part of the order data 404.

Capping

A capping station 420 is used to cap or seal container 402. In some embodiments, the capping station 420 includes a capping device to secure container 402 with a type of cap in accordance with a preference (e.g., a preference regarding child resistance that can be defined by for example, a patient, plan sponsor, or a prescriber). The cap device 420 applies the caps to a predetermined torque standard that allows for easy removal. Cap-maps are used to validate that the proper torque has been reached and, if not, a secondary inspection by a pharmacist is required.

Laser Etching

The pharmacy system 400 also includes a laser etching station 422 that etches a message and/or image into the cap. In an example embodiment, the etching station 422 can be physically integrated with the capping station 420. In addition to laser etching, etching station 422 can include other forms of marking the top of the container 402. For example, station 422 can mark the tops of the containers 402 with ink or labels that have been pre-marked with ink or otherwise.

Unloading

The pharmacy system 400 also includes an unloading station 424. Generally, there are two types of unloading. The first is smart unloading, which matches the container 402 to an order or literature in sequential order that pertains to the same order for multiple containers. The second unloading type is non-sequential unloading that allows the container 402 and literature to be married up at a later time.

Bottle Table

Bottle tables 426 are used for vertical storage of containers 402 that are sequentially parts of the same order. The bottle table 426 will store up to four containers 402 and is used to marry up parts of an order that can be processed at different locations, times, or areas of the pharmacy system 400. The purpose then is to bring all the containers 402 together and release the containers 402 together as an order in a sequential fashion for further processing or preparing the order for shipping.

Unit-of-Use

The system 400 includes a unit-of-use station 428 that temporarily stores, monitors, labels and/or dispenses unit-of-use products. In general, unit-of-use products are products that are delivered to a patient or member without being repackaged (e.g., after receipt from a pharmaceutical manufacturer or distributor) at the pharmacy. These products can include pills in a bottle or bottle-like container; pills in a blister pack; inhalers; gels; and the like. Products dispensed by the unit-of-use station 428 can be packaged individually or collectively for shipping or can be shipped in combination with other orders dispensed by other devices in the pharmacy system 400. The unit-of-use station 428 can include the system 100, 200 shown in FIGS. 1 and 2 for handling environmentally controlled drug order components, e.g., unit-of-use products 602 that need to be cooled until use. The unit of use station 428 can also include a separate system for processing unit-of-use products that are not environmentally sensitive.

The unit-of-use station 428 is used to take the manufacturer's bottles, boxes, or containers, and load them into a system that can sort, bag, or combine them with other equipment in the pharmacy, to complete the order. The end result of the unit-of-use station 428 is to have the bottle or container/box bagged and processed for mail delivery. The unit-of-use station 428 can at least partially operate in an environmentally controlled environment, e.g. a temperature-controlled setting that stores and process drugs to maintain the drug in the temperature range during processing and during delivery.

Accumulator

The accumulation station 430 accumulates various containers 402 in an order. The accumulation station 430 can accumulate containers 402 from various devices or areas of the pharmacy. For example, the accumulation station 430 can accumulate container and/or products from the unit-of-use station 428, the HVF filling station 412, the manual fulfilling station 414, and the review device 416, at the pharmacy system 400. The accumulation station 430 is used to group the containers and/or products prior to shipment to the member or otherwise. The accumulation station 430 shown in FIG. 4B is considered to be a horizontal accumulator, whereas the bottle table 426 can be considered to be a vertical bottle accumulator. The accumulation station 430 can receive an order component from the system 100, which is enclosed with coolant sufficient to allow delivery of the order via mail, other common carrier, courier, drone delivery, or otherwise within the temperature range.

Order Sorter

The order sorter 432 receives containers 402 from the accumulation station 430 and combines the order components, e.g., unit-of-use products, bottles, vials, and the like into an order that can be packaged and shipped in the mail system.

Packaging

The pharmacy system 400 also includes a number of wrap seal or packaging devices 434 that package the various components of an order together. The packing device 434 packages an order in preparation for shipping the order. The packing device 434 boxes, bags, sealed coolers or otherwise packages the fulfilled order for delivery. The packing device 434 also places inserts into the packaging. Bulk orders can be shipped in a box, while other orders can be shipped in a bag, which can be a wrap seal bag. The packing device 434 can label the box or bag with the address and a recipient's name. The packing device 434 can sort the box or bag for mailing in an efficient manner (e.g., sort by delivery address). The packing device 434 can include ice or temperature sensitive elements for products which are to be kept within a temperature range during shipping in order to retain efficacy or otherwise.

As shown in FIG. 4B, the pharmacy system 400 includes multiple packaging devices 434 for packaging different types of orders at different stages of order processing. These packaging devices 434 can be different parts of the same device or can be different devices. Further, there can be more than one packaging device 434 at each depicted location of a packaging device 434. Generally, the packaging devices 434 packages containers 402 and other order materials from any combination of the automated dispensing device 412, the manual filling device 414, the review device 416, the imaging device 418, the cap device 420, the laser etching device 422, the unloading device 424, the container table device 426, the unit-of-use device 428, the accumulator device 430, and the order sorter device 432 at the pharmacy system 400.

Flat Belt Conveyor

After an order has been through the packaging device 434, a conveyor 436, e.g., a flat belt conveyor, transports the packaged order to from a packaging device 434 to the shipping manifest 438.

Shipping Manifest

The shipping manifest station 438 receives orders from the packaging device 434 and then ships the package through a carrier, postal mail, through a mail order delivery service that ships via group and/or air (e.g., UPS®, FedEx®, or DHL®), through delivery service, through a locker box at a shipping site (e.g., Amazon Locker® or a PO Box), or otherwise.

Figure 5:
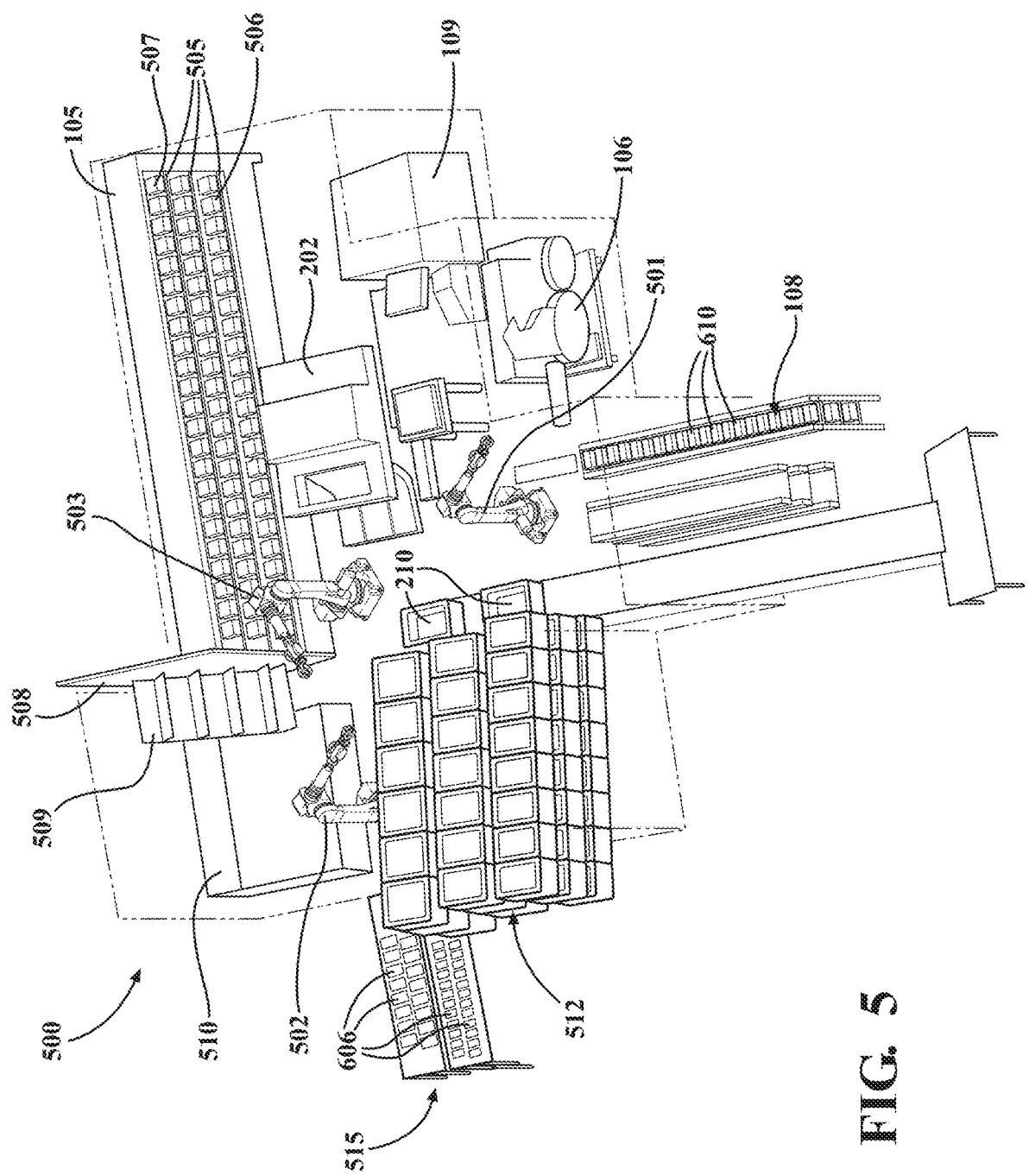
FIG. 5 is a diagram of an example implementation of a system for an automated pharmacy, according to an example embodiment.

FIGS. 5 and 6 show a diagram of an example implementation of an automated pharmacy system 500, which can be part of an automated pharmacy, e.g., a high-volume pharmacy. The system 500 uses three medication packing robots 501, 502, and 503 (as opposed to two robots in systems 100 and 200 discussed above), which individually access at least some distinct parts of the automated pharmacy with at least one point or area or station where two or all three of the robots 501, 502, 503 have joint access a part of the system 500. The robots 501, 502, 503 each have respective individual arcs of movement to travel between multiple stations and move respective medication containers (such as the unit-of-use products 602) or other related products between the stations. A station can be a location at which a function is performed to complete an order, e.g., in the automated pharmacy. The robots 501, 502, 503 can have at least six degrees of movement or more. The first robot 501 can be a unit-of-use robot that retrieves secondary items (for example, instruction papers or sharps products) for packaging in a container (such as an intermediate container) with the unit-of-use product 602. The second robot 502 operates to prepare a container (such as a cooler 210) for packaging. The third robot 503 retrieves the unit-of-use product 602 from a storage station 105 and places it in the cooler 210 as selected by the second robot 502. In an example embodiment, the third robot 503 is fixed in place and retrieves the unit-of-use product 602 from one end of the storage 105. The second robot 502 can select the environmental control devices, e.g., cold packs, to place in the container. In another embodiment, the third robot 503 can move longitudinally along the length of the storage 105.

The robots 501, 502 and 503 can each include end of arm tooling adapted to engage (e.g., grasp, grip suction, etc.) the unit-of-use product 602. The end of arm tooling includes various bag and box gripping solutions for various packaging such as bags, blister packs, boxes, bottles, ampules, syringes and the like drug containers. The robots 501, 502, 503 can each include one or more than one end of arm tools. By way of example, a first end of arm tool is adapted to engage a unit-of-use product 602, a second end of arm tool is adapted to engage a sharps box, a third end of arm tool is adapted to engage a cooler 210, a fourth end of arm tool is adapted to engage a lid for the cooler 120, a fifth end of arm tool is adapted to engage a bag containing the unit-of-use product 602, and a sixth arm is adapted to engage paperwork associated with a pharmaceutical order. The robots 501, 502, 503 can be robots that are adapted to physically interact with humans in a shared workspace.

The storage 105 is environmentally controlled, e.g., temperature and/or humidity controlled. The storage 105 can be a cooler. The storage 105 includes a plurality of tiers 505 (four being shown in the exemplary embodiment) that are separated from one another by longitudinally extending walls and that store the unit-of-use products 602 prior to them being selected by the robot 503. In the exemplary embodiment, the tiers 505 all hold different unit-of-use products 602. In some embodiments, the fewer or more than four tiers 505 may be provided, and some of those tiers 505 may contain similar unit-of-use products.

The storage 105 can be at least partially open at a side 506 facing the robot 503 so that the robot 503 can reach into the storage 105 through the open side. The tiers 505 can be loaded from the rear of the storage or from a first end 507 of the storage 105. In the exemplary embodiment, the tiers are sloped from the first end 507 towards a second end 508 located near the robot 503 such that the unit of use products 602 are guided along the tiers 505 towards the robot 503 with the assistance of gravity. In other words, the robot 503 can engage any of the unit-of-use products 602 at the second end 508 and, when one of the products 602 is removed from the storage 105, the other products 602 in that tier will automatically fall under the influence of gravity towards the second end 508, thereby putting a next sequential one of the products 602 in a ready-to-pick position adjacent the robot 503. In some embodiments, the tiers 505 may include conveyors for delivering the unit-of-use products 602 to the area of the robot 503.

A second end extension 509 is positioned at the second end 508 of the storage 105 and can engage empty boxes from the unit-of-use products 602 and deliver those boxes (or any other waste packaging) to a waste area 510, which is positioned adjacent the second end 508 of the storage 105.

The second robot 502 is positioned to interact with a cooler selection station, which includes a cooler storage rack 512. The cooler storage rack 512 can store a plurality of differently sized coolers into which the unit-of-use product 602 can be packaged with the required associated items. The second robot 502 can also retrieve the cooling packs 606 from a cooling pack station 515, which include a plurality of feed conveyors that can source a plurality of different types of cooling packs 606 to the second robot 502. The end of the conveyor is adjacent the robot 502 and the waste area 510 into which a further conveyor or robot 502 can drop waste, e.g., faulty cooling packs, packaging or boxes from the cooling pack station 515.

In operation, the first robot 501 can source the ancillary other items for the order and place them into the coolant package 210. In an example, one or more of the robots 501, 502, 503 pack the cooler 210 with the unit-of-use product 602, the cooling packs 606, and any additional order components, such as the printed literature, sharps if needed, filler material, and the like.

The controller 700 for the robots 501, 502, 503 can track the order and the individual items for the order as well as the inventory and location of the items in the pharmacy 500. The controller 700 can send orders to the robots 501, 502, 503 to fill an order including the locations of the items to be picked by the robots 501, 502, 503 and deposited into the cooler 210.

The present disclosure describes some embodiments with regard to a unit-of-use product. A unit-of-use product is made for dispensing a medication to a patient without product packaging modification (or with minimal product packaging modification) except for labeling with patient information. Unit-of-use products can include a full course of medicine to be taken by a patient, for example, an entire prescription (e.g., a thirty-day supply, a sixty-day supply, or a ninety-day supply). The unit-of-use products contain known quantities of medication in packages that are closed and sealed by, for example, the pharmaceutical manufacturer. Dispensing unit-of-use products greatly limits the need for manual or automated filling of open prescription containers with medication units that are first counted and then sealed at the pharmacy.

Various embodiments described herein use two or more robots for order fulfillment. The robots are each responsible for their individual areas or volumes of action and interact with each other. The interaction can be overlapping areas (e.g., radius) of movement. For example, a first robot can retrieve a shipping container and a second robot can retrieve the object that is part of the order from an environmentally controlled storage. In an example embodiment, another robot can place coolant in the shipping container or place the lid on the container. In an example embodiment, the first robot or a third robot can thereafter move the shipping container storing the object to a shipping station. In an example embodiment, the shipping container storing the object to a shipping station is positioned on a conveyor that moves the filled shipping container to the shipping station.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method can be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set can be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information, but information transmitted from element A to element B is relevant to the illustration, the arrow can point from element A to element B. This unidirectional arrow does not imply that no other information is transmitted from element B to element A. Further, for information sent from element A to element B, element B can send requests for, or receipt acknowledgements of, the information to element A.

In this application, including the definitions below, the term "module" or the term "controller" can be replaced with the term "circuit." The term "module" can refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module or other physical element in the pharmacy system can include one or more interface circuits. In some examples, the interface circuit(s) can implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4. For example, the interface circuits allow the robots to communicate with a controller, with each other or with other devices.

The module can communicate with other modules using the interface circuit(s). Although the module can be depicted in the present disclosure as logically communicating directly with other modules, in various implementations the module can actually communicate via a communications system. The communications system includes physical and/or virtual networking equipment such as hubs, switches, routers, and gateways. In some implementations, the communications system connects to or traverses a wide area network (WAN) such as the Internet. For example, the communications system can include multiple LANs connected to each other over the Internet or point-to-point leased lines using technologies including Multiprotocol Label Switching (MPLS) and virtual private networks (VPNs).

In various implementations, the functionality of the module can be distributed among multiple modules that are connected via the communications system. For example, multiple modules can implement the same functionality distributed by a load balancing system. In a further example, the functionality of the module can be split between a server (also known as remote, or cloud) module and a client (or, user) module.

Some or all hardware features of a module can be defined using a language for hardware description, such as IEEE Standard 1364-2005 (commonly called "Verilog") and IEEE Standard 1076-2008 (commonly called "VHDL"). The hardware description language can be used to manufacture and/or program a hardware circuit. In some implementations, some or all features of a module can be defined by a language, such as IEEE 1666-2005 (commonly called "SystemC"), that encompasses both code, as described below, and hardware description.

The term code, as used above, can include software, firmware, and/or microcode, and can refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The robots described herein include memory circuits to store control instructions and order information. The term computer-readable medium, as used herein, does not encompass transitory electrical or electromagnetic signals propagating through a medium (such as on a carrier wave); the term computer-readable medium can therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application can be partially or fully implemented by a special purpose computer created by configuring a computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The processors can control the robots, or any other device described herein. The computer programs can also include or rely on stored data. The computer programs can encompass a basic input/output system (BIOS) that interacts with hardware of the special purpose computer, device drivers that interact with particular devices of the special purpose computer, one or more operating systems, user applications, background services, background applications, etc.

The computer programs can include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code can be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The present systems and methods automate the dispensing of environmentally controlled drugs. A controller module, which may be located in the order processing device 134, can control robots, labelers, packagers, supply units and the like, to select, package and ship an environmentally controlled drug without the intervention of a human during these steps. The systems and methods can be part of a larger pharmacy, e.g., a specialty pharmacy or an automated pharmacy, but in an environmentally controlled part of such a larger pharmacy. The controller module can track an order from receipt from a medical care prescriber or a pharmacy benefits manager to delivery of a prepared package to the shipper. The prepared package includes the environmental controls for the drug.

The present system, as described herein, can include an environmentally controlled storage to hold drugs at a required environmental setting, a first robot to pick an ordered drug from the storage and package the drug, a second robot to receive the packaged ordered drug from the first robot and further package the packaged ordered drug for shipment with environmental controls to ensure that the ordered drug is maintained in the required environment during shipment from the automated pharmacy to the patient's location.

The environmentally controlled storage can be a temperature-controlled cooler with one or more temperature zones to store one or more temperature-controlled drugs within the required temperature range. The zones can have different temperature ranges. The cooler can store drugs at a lower temperature than room temperature and above freezing.

The first robot can be moveable in six dimensions and adapted to grip and move the ordered drug from the storage. The first robot can have a grasper hand or can rely on suction cups to engage the ordered drug, which can be a unit-of-use product. The first robot can move the ordered drug between multiple stations in the pharmacy. The stations can include bar code reader to check that the correct drug is selected from the storage. The ordered drug can then be moved to a labeler, which can apply a label to the ordered drug. The label can be printed at the labeler and adhered to the package. The label includes the type of drug, dosage, the patient name and address, pharmacy name, prescription number and other data. The first robot can move to other stations, such as a temperature sensing card dispenser, a sharps box feeder, a paperwork feeder, and envelope feeder and a packager. In an example, the ordered drug is moved to the labeler and then to the packager and placed in a package. The first robot can then retrieve the other order components from the other stations, i.e., the temperature sensing card dispenser, the sharps box feeder, the paperwork feeder, and the envelope feeder. The packager can then seal the ordered drug with the other order components in a package, e.g., a sealable bag.

The second robot has access to the packager and can retrieve a sealed package therefrom. The second robot can place the sealed package in an environmentally controlled determined structure that can ensure the ordered drug arrives at the patient location while maintaining the required environmental control. The second robot has access to a plurality of different shipment structures, i.e., differently sized coolers, different types or quantities of coolant. The second robot picks a correct shipment structure and places the sealed package therein. The second robot can then pick and place an ice pack or cooling gel in the shipment structure. Additional packaging can be added, if needed, to fill the shipment structure. A lid that is appropriate to the shipment structure is selected to enclose the sealed drug package and the coolant. The shipment structure is then secured for shipment, e.g., taped shut and labeled. The shipment package can be on a conveyor when secured and moved to a shipment site, which can or cannot be temperature controlled.

As described herein the first robot engages the drug to prepare a preliminary package including the drug and other order components. The second robot receives the preliminary package and packages that for shipment with the needed temperature control apparatus to ensure that the preliminary package is environmentally controlled during shipment. Shipment can be made through a common carrier once the order is packaged to provide the environmental control.

Example embodiments as described herein are directed to filling medication orders with environmentally controlled drugs, However, the systems and methods described herein may be adapted to complete orders for other environmentally controlled objects. An order is generated for an automated fulfillment system, e.g., a high-volume fulfillment system. A high-volume fulfillment system can include automatic object dispensing systems to carry out the dispensing of the objects automatically at a rapid rate. The objects can be ingestable or perishable. In the fulfillment system, an object can require environmental control while in storage and during shipping. The order can include more than one object for fulfillment. Each object in an order is an order component of the total order. An example of a controlled environment in the fulfillment system is one that maintains a required temperature range and/or humidity range. The controlled environment can be a lowered temperature. By way of example, a certain object requires a storage at a temperature less than room temperature but greater than freezing. The objects can be dispensed at various sections of the automated fulfillment system. Some orders can require manual handling of certain order components. Some order components can be filled automatically by filling machinery. The system can include at least two robots to retrieve, package, and prepare for shipping the order with an environmentally controlled object.

What is claimed is:

1. A temperature-controlled medication packaging system, comprising:
a storage including a temperature-controlled interior containing at least one medication;

a temperature sensor supply including at least one temperature sensor;
a first robot adapted to retrieve the at least one medication and the at least one temperature sensor and to deliver the at least one medication and the at least one temperature sensor to a packager;
the packager being adapted to produce an intermediate package containing the at least one medication and the at least one temperature sensor;
at least one cooler supply including at least one cooler;
at least one coolant supply including at least one coolant; and
a second robot adapted to deliver the intermediate package and the at least one cooler and the at least one coolant to a finisher.

2. The temperature-controlled medication packaging system as set forth in claim 1, wherein the at least one coolant includes at least two different coolants having different cooling capabilities, and wherein the second robot is adapted to select one of the at least two different coolants based on at least the type of medication in the intermediate package and on a destination for the medication.

3. The temperature-controlled medication packaging system as set forth in claim 2, wherein the at least one cooler includes at least two differently sized coolers, and wherein the second robot is adapted to select one of the at least two differently sized coolers based on the at least one medication in the intermediate package and based on a size of the selected one of the at least two different coolants.

4. The temperature-controlled medication packaging system as set forth in claim 1, wherein the first robot is further adapted to retrieve a sharps box from a sharps box feeder and deliver the sharps box to the packager.

5. The temperature-controlled medication packaging system as set forth in claim 1, wherein the first robot is further adapted to retrieve paperwork that includes drug information from a paperwork producer and to deliver the paperwork to the packager.

6. A method of producing a temperature-controlled medication package, comprising the steps of:
using a first robot, retrieving a medication from an environmentally-controlled storage and delivering the medication to a holding area;
using a second robot, retrieving the medication from the holding area and a shipping container and at least one coolant and delivering the medication and the shipping container and the coolant to a finisher; and
packaging the medication and coolant into the shipping container.

7. The method as set forth in claim 6, wherein the holding area is a packager and further including the step of at the packager, packaging the medication into an intermediate package.

8. The method as set forth in claim 7, further including the steps of:
using the first robot, retrieving a temperature sensor and delivering the temperature sensor to the packager; and
at the packager, packaging the temperature sensor with the medication in the intermediate package.

9. The method as set forth in claim 8, further including the steps of:
using the first robot, retrieving a sharps container and delivering the sharps container to the packager; and
at the packager, packaging the sharps container into the intermediate package.

10. The method as set forth in claim 8, further including the steps of:
using the first robot, retrieving paperwork from a paperwork producer and delivering the paperwork to the packager; and
at the packager, packaging the paperwork into the intermediate package.

11. The method as set forth in claim 8, further including the step of, with the second robot, inserting the intermediate package and the coolant and a filler into the cooler and placing a lid on the cooler.

12. The method as set forth in claim 11, further including the step of, with the second robot, selecting the at least one coolant out of at least two different types of coolants that have different cooling capabilities.

13. The method as set forth in claim 6, further including the step of, using the second robot, retrieving a cooler and delivering the cooler to the finisher.

14. The method as set forth in claim 13, further including the step of, using the second robot, selecting the cooler out of at least two different types of coolers that have different sizes.

15. A temperature-controlled medication packaging system, comprising:
a storage including a temperature-controlled interior containing at least one medication;
a first robot adapted to retrieve the at least one medication from the storage and to retrieve at least one of a temperature sensor, paperwork, and a sharps box and adapted to deliver the at least one of the temperature sensor, the paperwork, and the sharps box to a packager;
the packager being adapted to produce an intermediate package that contains the at least one medication and the at least one of the temperature sensor, the paperwork, and the sharps box;
at least one cooler supply including at least one cooler;
at least one coolant supply including at least one coolant; and
a second robot adapted to deliver the intermediate package and the at least one cooler and the at least one coolant to a finisher.

16. The temperature-controlled medication packaging system as set forth in claim 15, wherein the at least one cooler supply includes coolers of at least two types and wherein the second robot is adapted to select one of the at least two types of coolers.

17. The temperature-controlled medication packaging system as set forth in claim 15, wherein the at least one coolant supply includes at least two types of coolants that have different cooling capabilities and wherein the second robot is adapted to select one of the at least two types of coolants.

18. The temperature-controlled medication packaging system as set forth in claim 15, wherein the first robot is adapted to retrieve at least two of the temperature sensor, the paperwork, and the sharps box.

19. The temperature-controlled medication packaging system as set forth in claim 18, wherein the first robot is configured to retrieve all three of the temperature sensor, the paperwork, and the sharps box.

20. The temperature-controlled medication packaging system as set forth in claim 15, wherein the storage includes a curtain and wherein the first robot is adapted to reach through the curtain to retrieve the at least one medication.

* * * * *